(12) United States Patent
Hein et al.

(10) Patent No.: US 6,759,219 B2
(45) Date of Patent: Jul. 6, 2004

(54) METHODS FOR THE BIOSYNTHESIS OF POLYESTERS

(75) Inventors: Silke Hein, Münster (DE); Brigitte Söhling, Halle (DE); Gerhard Gottschalk, Nörten-Hardenberg (DE); Alexander Steinbüchel, Altenberge (DE)

(73) Assignee: Metabolix, Inc., Cambridge, MA (US)

( * ) Notice: Subject to any disclaimer, the term of this patent is extended or adjusted under 35 U.S.C. 154(b) by 0 days.

(21) Appl. No.: 09/380,773

(22) PCT Filed: Mar. 3, 1997

(86) PCT No.: PCT/US97/03994

§ 371 (c)(1),
(2), (4) Date: Sep. 3, 1999

(87) PCT Pub. No.: WO98/39453

PCT Pub. Date: Sep. 11, 1998

(65) Prior Publication Data

US 2003/0113884 A1 Jun. 19, 2003

(51) Int. Cl.$^7$ ............................. C12P 7/62; C12N 9/10; C12N 9/14; C12N 1/20; C07H 21/04
(52) U.S. Cl. ...................... 435/135; 435/141; 435/146; 435/170; 435/183; 435/189; 435/195; 435/193; 435/252.3; 435/320.1; 435/71.1; 536/23.2; 536/23.1

(58) Field of Search .............................. 435/135, 172.3, 435/252.3, 320.1, 252.8, 23.2; 536/141, 146, 170, 183, 195, 193, 252.3, 320.1, 71.1, 23.2, 23.1

(56) References Cited

U.S. PATENT DOCUMENTS

| 5,512,468 A | * | 4/1996 | Greener | 435/172.3 |
| 5,518,907 A | | 5/1996 | Dennis | 435/141 |
| 6,117,658 A | * | 9/2000 | Dennis et al. | 435/135 |

FOREIGN PATENT DOCUMENTS

| WO | WO 93/06225 | 4/1993 | C12P/7/44 |
| WO | WO 95/21257 | 8/1995 | C12N/15/52 |

OTHER PUBLICATIONS

Chemical Abstracts, vol. 127, No. 219607, Hein et al., "Biosynthesis of poly(4–hydroxybutyric acid) by recombinant strains of *Escherichia Coli*".

* cited by examiner

Primary Examiner—Ponnathapu Achutamurthy
Assistant Examiner—Yong D. Pak
(74) Attorney, Agent, or Firm—Pabst Patent Group LLP

(57) ABSTRACT

Coexpression of a polyhydroxyalkanoic acid synthase and either a fatty acid: acyl-CoA transferase or an acyl-CoA synthetase in cells enables the biosynthesis of polyester materials. Plasmids, bacteria, materials, and methods for the preparation of polyesters are disclosed.

25 Claims, No Drawings

SEQUENCE LISTING

<160> NUMBER OF SEQ ID NOS: 2

<210> SEQ ID NO 1
<211> LENGTH: 2768
<212> TYPE: DNA
<213> ORGANISM: Ralstonia eutropha

<400> SEQUENCE: 1

```
cccgggcaag taccttgccg acatctatgc gctggcgcgc acgcgcctgg cgcgcgccgg      60
ctgtaccgag gtctacggcg gcgacgcctg caccgtggcc gacgccggtc gcttctactc     120
ctatcggcgc gatggcgtga ccggccgcat ggccagcctg gtctggctgg cggactgagc     180
ccgccgctgc ctcactcgtc cttgccctg gccgcctgcg cgcgctcggc ttcagccttg      240
cgtcggcggc ggccgggcgt gcccatgatg tagagcacca cgccaccggc gccatgccat     300
acatcaggaa ggtggcaacg cctgccacca cgttgtgctc ggtgatcgcc atcatcagcg     360
ccacgtagag ccagccaatg gccacgatgt acatcaaaaa ttcatccttc tcgcctatgc     420 tctgggcct cggcagatgc gagcgctgca taccgtccgg taggtcggga agcgtgcagt     480
gccgaggcgg attcccgcat tgacagcgcg tgcgttgcaa ggcaacaatg gactcaaatg     540
tctcggaatc gctgacgatt cccaggtttc tccggcaagc atagcgcatg gcgtctccat     600
gcgagaatgt cgcgcttgcc ggataaaagg ggagccgcta tcggaatgga cgcaagccac     660
ggccgcagca ggtgcggtcg agggcttcca gccagttcca gggcagatgt gccggcagac     720
cctcccgctt tggggaggc gcaagccggg tccattcgga tagcatctcc ccatgcaaag     780
tgccggccag ggcaatgccc ggagccggtt cgaatagtga cggcagagag acaatcaaat     840
catggcgacc ggcaaaggcg cggcagcttc cacgcaggaa ggcaagtccc aaccattcaa     900
ggtcacgccg gggccattcg atccagccac atggctgaa tggtcccgcc agtggcaggg     960
cactgaaggc aacggccacg cggccgcgtc cggcattccg ggcctggatg cgctggcagg    1020
cgtcaagatc gcgccggcgc agctgggtga tatccagcag cgctacatga aggacttctc    1080
agcgctgtgg caggccatgg ccgagggcaa ggccgaggcc accggtccgc tgcacgaccg    1140
gcgcttcgcc ggcgacgcat ggcgcaccaa cctcccatat cgcttcgctg ccgcgttcta    1200
cctgctcaat gcgcgcgcct tgaccgagct ggccgatgcc gtcgaggccg atgccaagac    1260
ccgccagcgc atccgcttcg cgatctcgca atgggtcgat gcgatgtcgc ccgccaactt    1320
ccttgccacc aatcccgagg cgcagcgcct gctgatcgag tcgggcggcg aatcgctgcg    1380
tgccggcgtg cgcaacatga tggaagacct gacacgcggc aagatctcgc agaccgacga    1440
```

-continued

```
gagcgcgttt gaggtcggcc gcaatgtcgc ggtgaccgaa ggcgccgtgg tcttcgagaa    1500
cgagtacttc cagctgttgc agtacaagcc gctgaccgac aaggtgcacg cgcgcccgct    1560
gctgatggtg ccgccgtgca tcaacaagta ctacatcctg gacctgcagc cggagagctc    1620
gctggtgcgc catgtggtgg agcagggaca tacggtgttt ctggtgtcgt ggcgcaatcc    1680
ggacgccagc atggccggca gcacctggga cgactacatc gagcacgcgg ccatccgcgc    1740
catcgaagtc gcgcgcgaca tcagcggcca ggacaagatc aacgtgctcg gcttctgcgt    1800
gggcggcacc attgtctcga ccgcgctggc ggtgctggcc gcgcgcggcg agcacccggc    1860
cgccagcgtc acgctgctga ccacgctgct ggactttgcc gacacgggca tcctcgacgt    1920
ctttgtcgac gagggccatg tgcagttgcg cgaggccacg ctgggcggcg cgccggcgc    1980 gccgtgcgcg ctgctgcgcg ccttgagct ggccaatacc ttctcgttct gcgcccgaa    2040 cgacctggtg tggaactacg tggtcgacaa ctacctgaag gcaacacgc cggtgccgtt    2100 cgacctgctg ttctggaacg cgacgccac caacctgccg gggccgtggt actgctggta    2160
cctgcgccac acctacctgc agaacgagct caaggtaccg ggcaagctga ccgtgtgcgg    2220
cgtgccggtg gacctggcca gcatcgacgt gccgacctat atctacggct cgcgcgaaga    2280
ccatatcgtg ccgtggaccg cggcctatgc ctcgaccgcg ctgctggcga acaagctgcg    2340
cttcgtgctg ggtgcgtcgg gccatatcgc cggtgtgatc aacccgccgg ccaagaacaa    2400
gcgcagccac tggactaacg atgcgctgcc ggagtcgccg cagcaatggc tggccggcgc    2460
catcgagcat cacggcagct ggtggccgga ctggaccgca tggctggccg ggcaggccgg    2520
cgcgaaacgc gccgcgcccg ccaactatgg caatgcgcgc tatcgcgcaa tcgaacccgc    2580
gcctgggcga tacgtcaaag ccaaggcatg acgcttgcat gagtgccggc gtgcgtcatg    2640
cacggcgccg gcaggcctgc aggttccctc ccgtttccat tgaaaggact acacaatgac    2700
tgacgttgtc atcgtatccg ccgcccgcac cgcggtcggc aagtttggcg gctcgctggc    2760
caagatcc                                                             2768
```

<210> SEQ ID NO 2
<211> LENGTH: 7120
<212> TYPE: DNA
<213> ORGANISM: Clostridium kluyveri

<400> SEQUENCE: 2

```
agcttgaaaa aatattggta aaatccgaag aagattttag tgtggtaaaa agtatattga     60
ataagtattt aacaagacag gatagggagg agataacttt tatggagtgg gaagagatat    120
ataaagagaa actggtaact gcagaaaaag ctgtttcaaa aatagaaaac catagcaggg    180 tagttttgc acatgcagta ggagaacccg tagatttagt aaatgcacta gttaaaaata    240
aggataatta tataggacta gaaatagttc acatggtagc tatgggcaaa ggtgtatata    300
caaaagaggg tatgcaaaga catttagac ataatgcttt gtttgtaggc ggatctacta    360
gagatgcagt aaattcagga agagcagttt atacaccttg ttttttctat gaagtgccaa    420
gtttgtttaa agaaaaacgt tgcctgtag atgtagcact tattcaggta agtgagccag    480
ataaatatgg ctactgcagt tttggagttt ccaatgacta taccaagcca gcagcagaaa    540
gtgctaagct tgtaattgca gaagtgaata aaaacatgcc aagaactctt ggagattctt    600
ttatacatgt atcagatatt gattatatag tggaagcttc acacccattg ttagaattgc    660
agcctcctaa attgggagat gtagaaaaag ccataggaga aaactgtgca tctttaattg    720
```

-continued

```
aagatggagc tactcttcag cttggaatag gtgctatacc agatgcggta cttttattct      780
taaagaacaa aaagaattta ggaatacatt ctgagatgat atcagatggt gtgatggaac      840
tggtgaaggc aggggttatc aataacaaga aaaagaccct ccatccaggc aaaatagttg      900
taacattttt aatgggaaca aaaaaattat atgattttgt aaacaataat ccaatggtag      960
aaacttattc tgtagattat gtaaataatc cactggtaat tatgaaaaat gacaatatgg     1020
tttcaataaa ttcttgtgtt caagtagact taatgggaca agtatgttct gaaagtatag     1080
gattgaaaca gataagtgga gtgggaggcc aggtagattt tattagagga gctaatctat     1140
caaagggtgg aaaggctatt atagctatac cttccacagc tggaaaagga aaagtttcaa     1200
gaataactcc acttctagat actggtgctg cagttacaac ttctagaaat gaagtagatt     1260
atgtagttac tgaatatggt gttgctcatc ttaagggcaa aactttaaga aatagggcaa     1320
gagctctaat aaatatcgct catccaaaat tcagagaatc attaatgaat gaatttaaaa     1380
agagatttta gaatttattt atgattttta gttcactttt atatgaaggt gtaactaaaa     1440
ataagaattc aattgtagtt aatttaacga gatattgtat taaatttaac aaaatgaggc     1500
ttaatttata ggggaggaat gtaaattgaa aaaagggtat atatttattt tattgacggc     1560
aatattttat agcactcagg agatttcagg aaaaatgtta gctcaaaagg gtgctatgga     1620
tccatttcaa gttatgatga ttgtattttt aataggtgcg ataatactgc ttcctatggc     1680
tgtgaaagat ataaaagtca aaaagcttaa acttactggt aatgatttag ggtatcttgc     1740
tctttgtgga atactggcag tatcaatttc tatgtctatg ctccagtttg cagttactta     1800
tactaaggca tctactgcgg cggtattatt ctgtactaat gcagtattta ccataccttt     1860
tgcatatttc atattaaaag aaaagataaa agggattacc atagtttcta ttattgtttc     1920
attgattggt gtagttataa tatttaatcc tgcaaaggtt atggaaggta ttggaggaag     1980
cagggattta ataggaatat gtttcgcact tgtagcagct gtagtttggt ctttatacac     2040
agtaataagt aaaagagaaa ttgagattta tggaggatat gttttttaatt gcatctcttt     2100 cttcttcggg gtaatagcac ttttaattct cttagtagtt actggcagac caatattcag     2160
tggaattact ttaaataata ttctagtgct tttatacatg ggtattttta taaaagctgt     2220
tggttatata tgttatcttg gtgccataaa agagacttcc gctgtaactg catctacagt     2280
ttttcttata aaacctgcac tagctacagt acttgcaatt ttaattttag gtgaaagtat     2340
agaggtaaat gtagttatag gtattgtgtt tataattata ggttctatta taaattattc     2400
tagtaataaa aaggcaaatg atttaaaaaa agttgctaat actagtagtg cagagagtta     2460
attaatagga agtttgtaaa ttaataatat tttaactatt tgtgaggcga ttaaatgagt     2520
aaagggataa agaattcaca attgaaaaaa agaatgtaaa aggctagtaa tgtggcagaa     2580
aagattgaag agaagttgaa aaaacagat aaggttgttg aaaaggcagc tgaggttact     2640
gaaaaacgaa ttagaaactt gaagcttcag gaaaagttg taacagcaga tgtggcagct     2700
gatatgatag aaaacggtat gattgttgca attagcggat ttactccttc cgggtatcct     2760
aaagaagtac ctaaagcatt gactaaaaaa gttaatgcct tagaggaaga attcaaggta     2820
acactttata caggttcatc tacaggagcc gatatagacg gagaatgggc aaaagcagga     2880
ataatagaaa gaagaattcc atatcagaca aattctgata tgaggaaaaa aataaatgat     2940
ggttctatta gtatgctga tatgcattta agccatatgg ctcaatatat taattattct     3000
gtaattccta agtagatat agctataata gaggcagtag ctattacaga agaagggat     3060 attattccctt caacaggaat tggaaataca gctactttg tggaaaatgc agataaggta     3120
```

```
atagtggaaa ttaatgaggc tcaaccgctt gaattggaag gtatggcaga tatatataca      3180
ttaaaaaacc ctccaagaag agagcccata cctatagtta atgcaggcaa taggataggg      3240
accacatatg tgacctgtgg ttctgaaaaa atatgcgcta tagtgatgac aaatacccag      3300
gataaaacaa gacctcttac agaagtgtct cctgtatctc aggctatatc cgataatctt      3360
ataggatttt taaataaaga ggttgaagag ggaaaattac ctaagaacct gcttcctata      3420
cagtcaggag ttggaagtgt agcaaatgca gttttggccg gactttgtga atcaaatttt      3480
aaaaatttga gttgttatac agaagttata caggattcta tgctgaagct tataaaatgt      3540
ggtaaagcag atgtggtgtc aggcacttcc ataagtcctt caccggagat gttgcctgag      3600
ttcataaagg acataaattt ctttagagaa aagatagtat taagaccaca ggaaataagt      3660
aataatccag agatagcaag aagaatagga gttatatcca taaacactgc tttggaagta      3720
gatatatatg gtaatgtaaa ctccactcat gttatgggaa gcaaaatgat gaatggtata      3780
ggcggttctg gagactttgc cagaaatgca tatttgacta tattcactac agagtctatc      3840
gccaaaaaag gagatatatc atctatagtt cctatggtat cccatgtgga tcatacagaa      3900
catgatgtaa tggtaattgt tacagaacag ggagtagcag atttaagagg tctttctcct      3960
agggaaaagg ccgtggctat aatagaaaat tgtgttcatc ctgattacaa ggatatgctt      4020
atggaatatt ttgaagaggc ttgtaagtca tcaggtggaa atacaccaca taatcttgaa      4080
aaagctcttt cctggcatac aaaatttata aaaactggta gtatgaaata aatatcaaca      4140
agtataatac aaaaatttta aatatataaa acatttattt aggaggaaaa atatgagtaa      4200
tgaagtatct ataaaagaat taattgaaaa ggcaaaggcg gcacaaaaaa aattggaagc      4260
ctatagtcaa gaacaagttg atgtactagt aaaagcacta ggaaaagtgg tttatgataa      4320
tgcagaaatg tttgcaaaag aagcagttga agaaacagaa atgggtgttt atgaagataa      4380
agtagctaaa tgtcatttga aatcaggagc tatttggaat catataaaag acaagaaaac      4440
tgtaggcata ataaaagaag aacctgaaag ggcacttgtt tatgttgcta agccaaaggg      4500
agttgtggca gctactacgc ctataactaa tccagtggta actccatatgt gtaatgcaat      4560 ggctgctata aagggcagaa atacaataat agtagcacca catcctaaag caaagaaagt      4620
ttcagctcat actgtagaac ttatgaatgc tgagcttaaa aaattgggag caccagaaaa      4680
tatcatacag atagtagaag caccatcaag agaagctgct aaggaactta tggaaagtgc      4740
tgatgtagtt attgctacag gcggtgctgg aagagtaaaa gctgcttact ccagtggaag      4800
accagcttat ggcgttggac ctggaaattc acaggtaata gttgataagg gatacgatta      4860
taacaaagct gcacaggata taataacagg aagaaaatat gacaatggaa ttatatgttc      4920
ttcagagcaa tcagttatag ctcctgctga agattatgat aaggtaatag cagcttttgt      4980
agaaaatggg gcattctatg tagaagatga ggaaacagta gaaagtttta gatcaacttt      5040
atttaaagat ggaaaaataa acagcaagat tataggtaaa tccgtccaaa ttattgcgga      5100
tcttgcagga gtaaaagtac cagaaggtac taaggttata gtacttaagg gtaaaggtgc      5160
aggagaaaaa gatgtacttt gtaaagaaaa aatgtgtcca gttttagtag cattgaaata      5220
tgatactttt gaagaagcag ttgaaatagc tatggctaat tatatgtatg aaggagctgg      5280
tcatacagca ggcatacatt ctgacaatga cgagaacata agatatgcaa gaactgtatt      5340
acctataagc agattagttg taaatcagcc tgcaactact gctggaggaa ctgtattacc      5400
tataagcaga ttagttgtaa atcagcctgc aactactgct ggaggaagtt tcaataatgg      5460
```

```
                                                  -continued atttaaccct actactacac taggctgcgg atcatggggc agaaacagta tttcagaaaa     5520
tcttacttac gagcatctta taaatgtttc aagaataggg tatttcaata aagaagcaaa     5580
agttcctagc tatgaggaaa tatggggata agtcctgtta ttaaaaagta tataaggagg     5640
aaaaaatatg aagttattaa aattggcacc tgatgtttat aaatttgata ctgcagagga     5700
gtttatgaaa tactttaagg ttggaaaagg tgactttata cttactaatg aatttttata     5760
taaacctttc cttgagaaat tcaatgatgg tgcagatgct gtatttcagg agaaatatgg     5820
actcggtgaa ccttctgatg aaatgataaa caatataatt aaggatattg gagataaaca     5880
atataataga attattgctg taggggagg atctgtaata gatatagcca aaatcctcag      5940
tcttaagtat actgatgatt cattggattt gtttgaggga aaagtacctc ttgtaaaaaa     6000
caaagaatta attatagttc caactacatg tggaacaggt tcagaagtta caaatgtatc     6060
agttgcagaa ttaaagagaa gacatactaa aaaaggaatt gcttcagacg aattatatgc     6120
aacttatgca gtacttgtac cagaatttat aaaaggactt ccatataagt tttttgtaac     6180
cagctccgta gatgccttaa tacatgcaac agaagcttat gtatctccaa atgcaaatcc     6240
ttatactgat atgtttagtg taaaagctat ggagttaatt ttaaatggat acatgcaaat     6300
ggtagagaaa ggaaatgatt acagagttga aataattgag gattttgtta taggcagcaa     6360
ttatgcaggt atagcttttg gaaatgcagg agtgggagcg gttcacgcac tctcatatcc     6420
aataggcgga aattatcatg tgcctcatgg agaagcaaat tatctgtttt ttacagaaat     6480
atttaaaact tattatgaga aaaatccaaa tggcaagatt aaagatgtaa ataaactatt     6540
agcaggcata ctaaaatgtg atgaaagtga agcttatgac agtttatcac aactttaga     6600 taaattattg tcaagaaaac cattaagaga atatggaatg aaagaggaag aaattgaaac     6660
ttttgctgat tcagtaatag aaggacagca gagactgttg gtaaacaatt atgaaccttt     6720
ttcaagagaa gacatagtaa acacatataa aaagttatat taatatgtaa cctacaatca     6780
ttaaatatcc catcttaaga gggcatttcc atattgtgaa atgtcctctt ttttatctaa     6840
ataataccgt tctattacta agaaacacct aatataacat ataaggataa tatttctgac     6900
atagtatttg aaaaagtttt catcaatttt gtgacttcat gatataataa tagtggtaga     6960
aaatgattct tatgcgatga acataagaat cacttgataa taatcttaga tgggaggtgt     7020
gtataaaggt gaaaatggat tttgctctta atttaactca ggaacaaaga ttggccatga     7080
cccaggaaat gcaattgtcc ataaagttgc tccaaatgtc                          7120
```

METHODS FOR THE BIOSYNTHESIS OF POLYESTERS

FIELD OF THE INVENTION

The invention relates generally to the field of molecular biology. Certain embodiments entail materials and methods suitable for the biosynthesis of biopolymers, namely polyhydroxyalkanoic acid polymers.

BACKGROUND OF THE INVENTION

The production of intracellular polyesters belonging to the class of polymers known as polyhydroxyalkanoates (polyhydroxyalkanoic acids) has been observed in a wide array of prokaryotic organisms (Anderson, A. J. and Dawes, E. A. (1990) *Microbiol. Rev.* 54:450–472; Steinbüchel, A. and Valentin, H. E. (1995) *FEMS Microbiol. Lett.* 128:219–228). The monomers composing the polyesters range in length from C4 (3-hydroxybutyrate) to C12 (3-hydroxydodecanoate) (Lageveen, R. G. et al. (1988) *Appl. Env. Microbiol.* 54:2924–2932). These polyesters have attracted considerable interest as they are biodegradable. Potential technical applications exist in industry and agriculture, as well as in medical devices and procedures (Hocking, P. J. and Marchessault, R. H. (1994) Biopolyesters. In: G. J. L. Griffin (Ed) Chemistry and technology of biodegradable polymers, Chapman & Hall, London, pp.48–96; Müller, H. M. and Seebach, D. (1993) *Angew. Chem.* 105:483–509). Additionally, this class of polyesters is attractive as a potential alternative to conventional petrochemical-derived plastics.

Polyhydroxyalkanoic acids are broadly characterized according to the monomers that constitute their backbone. Polymers composed of C4–C5 units are classified as short chain length (scl) polyhydroxyalkanoic acids; polymers containing monomers of C6 units and above are classified as medium chain length (mcl) polyhydroxyalkanoic acids. The primary structure of the polymer influences the physical properties of the polyester.

The metabolic pathways leading to the formation of polyhydroxyalkanoic acids have not been elucidated for all organisms. The most extensively studied polyhydroxyalkanoic acid biosynthetic pathway is that of Alcaligenes (Peoples, O. P. et al. (1989) *J. Biol. Chem.* 264:15298–15303; Valentin, H. E. et al. (1995) *Eur. J. Biochem.* 227:43–60). This organism is capable of forming either a homopolymer of C4 (polyhydroxybutyrate, PHB) or a co-polymer of C4–C5 (PHB-PHV, polyhydroxybutyrate-polyhydroxyvalerate) (Koyama, N. and Doi, Y. (1995) *Biotechnol. Lett.* 17:281–284). Hence, *A. eutrophus* is classified as a scl polyhydroxyalkanoic acid organism. Similarly, Pseudomonas species generate a polymer composed of monomers ranging in length from C6 to C12 (Timm, A. and Steinbüchel, A. (1990) *Appl. Environ. Microbiol.* 56:3360; Lageveen, R. G. et al. (1988) *Appl. Env. Microbiol.* 54:2924–2932), and are classified as mcl polyhydroxyalkanoic acid organisms.

The polymerization of the hydroxyacyl-CoA substrates is carried out by polyhydroxyalkanoic acid synthases. The substrate specificity of this class of enzyme varies across the spectrum of polyhydroxyalkanoic acid producing organisms. This variation in substrate specificity of polyhydroxyalkanoic acid synthases is supported by indirect evidence observed in heterologous expression studies (Lee, E. Y. et al. (1995) *Appl. Microbiol. Biotechnol.* 42:901–909; Timm, A. et al. (1990) *Appl. Microbiol. Biotechnol.* 33:296–301).

Hence, the structure of the backbone of the polymer is strongly influenced by the polyhydroxyalkanoic acid synthase responsible for its formation.

Fluorescent pseudomonads belonging to the rRNA homology group I can synthesize and accumulate large amounts of polyhydroxyalkanoic acids (PHA) composed of various saturated and unsaturated hydroxy fatty acids with carbon chain lengths ranging from 6 to 14 carbon atoms (Steinbüchel, A. and Valentin, H. E. (1992) *FEMS Microbiol. Rev.* 103:217). Polyhydroxyalkanoic acid isolated from these bacteria also contains constituents with functional groups such as branched, halogenated, aromatic or nitrile side-chains (Steinbüchel and Valentin (1995 *FEMS Microbiol. Lett.* 128:219–228). The composition of polyhydroxyalkanoic acid depends on the polyhydroxyalkanoic acid polymerase system the carbon source, and the metabolic routes (Anderson, A. J. and Dawes, E. A. (1990) *Microbiol. Rev.* 54:450–472; Eggink et al. (1992) *FEMS Microbiol. Rev.* 105:759; Huisman, A. M. et al. (1989) *Appl. Microbiol. Biotechnol.* 55:1949–1954; Lenz, O. et al. (1992) *J. Bacteriol.* 176:4385–4393; Steinbüchel, A. and Valentin, H. E. (1995) *FEMS Microbiol. Lett.* 128:219–228). In *P. putida*, at least three different metabolic routes occur for the synthesis of 3-hydroxyacyl CoA thioesters, which are the substrates of the polyhydroxyalkanoic acid synthase (Huijberts, G. N. M. et al. (1994) *J. Bacteriol.* 176:1661–1666): (i) β-oxidation is the main pathway when fatty acids are used as carbon source; (ii) De novo fatty acid biosynthesis is the main route during growth on carbon sources which are metabolized to acetyl-CoA, like gluconate, acetate or ethanol; and (iii) Chain elongation reaction, in which acyl-CoA is condensed with acetyl-CoA to the two carbon chain extended β-keto product which is then reduced to 3-hydroxyacyl-CoA. This latter pathway is involved in polyhydroxyalkanoic acid-synthesis during growth on hexanoate.

The polyhydroxyalkanoic acid synthase structural gene from Alcaligenes eutrophus (phaC$_{Ae}$) has been cloned and characterized at the molecular level in several laboratories (for a review see Steinbüchel, A. and Schlegel, H. G. (1991) *Mol. Microbiol.* 5:535–542; GenBank Accession number J05003). It was demonstrated that phaC$_{Ae}$ in combination with other genes conferred the ability to synthesize poly(3-hydroxybutyric acid) not only to many bacteria, which do not synthesize this polyester such as e.g. *Escherichia coli* (Steinbüchel, A. and Schlegel, H. G. (1991) *Mol. Microbiol.* 5:535–542) but also to *Saccharomyces cerevisiae* (Leaf, T. A. et al. (1996) *Microbiology* 142:1169–1180), plants such as *Arabidopsis thaliana* (Poirier, Y. et al. (1992) *Science* 256:520–523.) and *Gossypium hirsutum* (John, M. E. and Keller, G. (1996) *Proc. Natl. Acad. Sci. U.S.A.* 93:12768–12773), and even to cells from the insect *Spodoptera frugiperda* (Williams, M. D. et al. (1996) *Appl. Environ. Microbiol.* 62:2540–2546).

The development of biological systems that synthesize poly(4-hydroxybutyric acid), poly(3-hydroxybutyric acid-co-4-hydroxybutyric acid), and other polyester materials would be of great utility. Biological systems provide the potential to produce significant quantities of important materials, while utilizing inexpensive feedstocks and minimizing hazardous byproducts.

There exists a need for novel biosynthetic routes to polymers of potential commercial interest that do not rely on petroleum based starting materials Biological processes present an attractive alternative to chemical processes that produce potentially harmful byproducts while consuming non-renewable resources.

SUMMARY

This invention relates to materials and processes for preparing polyester materials. More particularly, the invention is related to materials and processes for the preparation of polyester materials, preferably poly(4-hydroxybutyric acid), poly(3-hydroxybutyric acid), and poly(3-hydroxybutyric acid-co-4-hydroxybutyric acid). The invention provides nucleic acid segments encoding a polyhydroxyalkanoic acid synthase protein and either a fatty acid:acyl-CoA transferase protein or an acyl-CoA synthetase protein, recombinant vectors, cells containing the nucleic acid segments, and methods for the preparation of polyester materials.

The scope of the present invention will be further apparent in light of the detailed descriptions provided below. However, it should be understood that the following detailed description and examples, while indicating preferred embodiments of the present invention, are given by way of illustration only since various changes and modifications within the spirit and scope of the present invention will become apparent to those of ordinary skill in the art from this detailed description.

Definitions

The following definitions are provided in order to aid those skilled in the art in understanding the detailed description of the present invention.

An "acyl-CoA synthetase" or "thiokinase" protein catalyzes the formation of a thioester linkage between the carboxyl group of a fatty acid and the sulfhydryl group of CoA.

An "acyl kinase" protein catalyzes the transfer of a phosphate group from ATP to a carboxylate group according to the reaction:

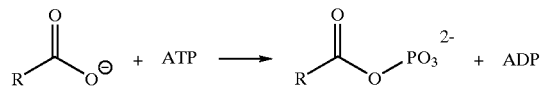

wherein R is an alkyl or hydroxyalkyl group.

"CoA" refers to coenzyme A.

The term "fatty acid:acyl-Co A transferase" refers to a protein that catalyzes an acyl group transfer according to the reaction:

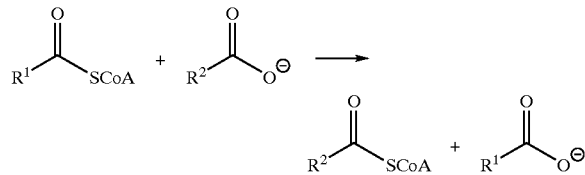

wherein $R^1$ and $R^2$ are alkyl or hydroxyalkyl groups. Groups $R^1$ and $R^2$ may further contain one or more double bonds, triple bonds, or aromatic groups.

"Copolyester" refers to a polyester material made from a two different monomeric building blocks. For example, poly(3-hydroxybutyric acid-co-4-hydroxybutyric acid) is a polyester made from 3-hydroxybutyric acid and 4-hydroxybutyric acid. The relative composition of the two monomeric building blocks in the copolyester can be variable. Copolyesters are commonly characterized by the relative percentages of the two monomeric building blocks. The percentage composition may affect the physical characteristics of the copolyester.

"Dimeric" refers to enzymes that are comprised of two protein molecule subunits. The two subunits may be identical (homodimeric) or different (heterodimeric) in sequence.

"Heterologous" refers to nucleotide segments not normally found in nature in the same organism.

"Homopolyester" refers to a polyester material made from a single monomeric building block. For example, poly(4-hydroxybutyric acid) is a polyester made from 4-hydroxybutyric acid.

A "4-hydroxybutyrate dehydrogenase" protein catalyzes the conversion of succinate semialdehyde to 4-hydroxybutyrate.

The combination of "2-methylcitrate dehydratase" protein and "2-methylisocitrate dehydratase" protein catalyzes the conversion of 2-methylcitrate to 2-methylisocitrate.

A "2-methylcitrate synthase" protein catalyzes the conversion of propionyl-CoA and oxaloacetate to 2-methylcitrate.

A "2-methylisocitrate lyase" protein catalyzes the conversion of 2-methylisocitrate to pyruvate and succinate.

The terms "microbe", "microorganism", and "microbial" refer to algae, bacteria, fungi, and protozoa.

"Monomeric" refers to enzymes that are comprised of a single protein molecule.

"Native" refers to two segments of nucleic acid naturally occurring in the same organism. For example, a native promoter is the promoter naturally found with a given gene in an organism.

"Nucleic acid" refers to deoxyribonucleic acid (DNA) and ribonucleic acid (RNA).

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

A "2-oxogluatarate decarboxylase" protein catalyzes the conversion of 2-oxoglutarate to succinate semialdehyde.

A "phosphotransacylase" protein catalyzes the transfer of a phosphorylated acyl group to CoA according to the reaction:

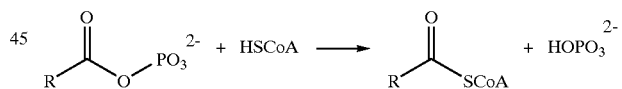

The phrases "polyhydroxyalkanoic acid biosynthetic genes" and "polyhydroxyalkanoic acid biosynthetic enzymes" refer to those genes or enzymes leading to anabolic reactions in the pathway of polyhydroxyalkanoic acid production.

The phrase "polyhydroxyalkanoate (PHA) synthase" refers to enzymes that convert hydroxyacyl-CoAs to polyhydroxyalkanoates and free CoA.

The term "promoter" or "promoter functional in bacteria" refer to a nucleotide sequence, usually found upstream (5') to a coding sequence, that controls expression of the coding sequence by controlling production of messenger RNA (mRNA) by providing the recognition site for RNA polymerase and/or other factors necessary for the start of transcription at the correct site. The promoters disclosed herein, and biologically functional equivalents thereof, are responsible for driving the transcription of coding sequences under their control when introduced into a bacterial cell, as demonstrated by their ability to produce mRNA.

The terms "recombinant vector" and "vector" refer to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner ("operatively linked"). Such recombinant DNA constructs or vectors are capable of introducing a 5' regulatory sequence or promoter region and a DNA sequence for a selected gene product into a cell in such a manner that the DNA sequence is transcribed into a functional mRNA which is translated and therefore expressed.

A "succinate-semialdehyde dehydrogenase" protein catalyzes the conversion of succinyl-CoA to succinate semialdehyde.

A "succinate:acetyl-CoA transferase" protein catalyzes the conversion of succinate to succinyl-CoA.

DETAILED DESCRIPTION OF ILLUSTRATIVE EMBODIMENTS

The present invention provides a novel method for the preparation of polyester materials. In one important embodiment, co-expression of a polyhydroxyalkanoic acid synthase gene and a fatty acid:acyl-CoA transferase gene in a cell enable the biosynthesis of poly(4-hydroxybutyric acid). In an alternative embodiment, the co-expression of a polyhydroxyalkanoic acid synthase gene and a fatty acid:acyl-CoA transferase gene in bacteria leads to the biosynthesis of poly(3-hydroxybutyric acid). In a further alternative embodiment, co-expression of a polyhydroxyalkanoic acid synthase gene and a fatty acid:acyl-CoA transferase gene in a cell enable the biosynthesis of the copolyester poly(3-hydroxybutyric acid-co-4-hydroxybutyric acid). In an alternative embodiment, co-expression of a polyhydroxyalkanoic acid synthase gene and a fatty acid:acyl-CoA transferase gene in a cell enable the biosynthesis of poly(4-hydroxybutyric acid).

Alternatively, the co-expression of a polyhydroxyalkanoic acid synthase gene and an acyl-CoA synthetase gene in a cell leads to the biosynthesis of poly(3-hydroxybutyric acid). In a further alternative embodiment, co-expression of a polyhydroxyalkanoic acid synthase gene and an acyl-CoA synthetase gene in a cell enable the biosynthesis of the copolyester poly(3-hydroxybutyric acid-co-4-hydroxybutyric acid). In an alternative embodiment, co-expression of a polyhydroxyalkanoic acid synthase gene and an acyl-CoA synthetase gene in a cell enable the biosynthesis of poly(4-hydroxybutyric acid).

In one important embodiment, the invention provides a nucleic acid segment that encodes a polyhydroxyalkanoic acid synthase protein, and that encodes a fatty acid:acyl-CoA transferase protein. The polyhydroxyalkanoic acid synthase protein may generally be any polyhydroxyalkanoic acid synthase protein suitable for the production of polyester materials according to the inventive processes. The polyhydroxyalkanoic acid synthase protein may be monomeric or dimeric. Monomeric polyhydroxyalkanoic acid synthase proteins include, but are not limited to, those from *Rhizobium meliloti, Alcaligenes eutrophus,* Alcaligenes sp., *Rhizobium etli, Paracoccus denitrificans,* Acinetobacter sp., *Rhodobacter sphaeroides, Meihylobacterium extorquens, Pseudomonas oleovorans, Pseudomonas aeruginosa, Rhodococcus ruber,* and *Zoogloea ramigera.* Dimeric polyhydroxyalkanoic acid synthase proteins include, but are not limited to, those from *Thiocystis violacea* and *Chromatium vinosum.* Preferably, the polyhydroxyalkanoic acid synthase protein is an *Alcaligenes euirophus* polyhydroxyalkanoic acid synthase protein, and more preferably, the *Alcaligenes eutrophus* polyhydroxyalkanoic acid synthase protein encoded by the *Alcaligenes eutrophus phaC* polyhydroxyalkanoic acid synthase structural gene. The fatty acid:acyl-CoA transferase protein may be any fatty acid:acyl-CoA transferase protein suitable for the preparation of polyester materials according to the inventive processes. Fatty acid:acyl-CoA transferase proteins include, but are not limited to, 4-hydroxybutyrate:acetyl-CoA transferase from *Clostridium aminobutyricum,* propionate:acyl-CoA transferase from *Clostridium propionicum,* and succinate:acyl-CoA transferase from *Clostridium kluyveri.* Preferably, the fatty acid:acyl-CoA transferase protein is a 4-hydroxybutyrate:acyl-CoA transferase protein, more preferably a *Clostridium kluyveri* 4-hydroxybutyrate:acyl-CoA transferase protein, and most preferably, the *Clostridium kluyveri* 4-hydroxybutyrate:acyl-CoA transferase protein encoded by the *Clostridium kluyveri orfZ* 4-hydroxybutyrate:acyl-CoA transferase structural gene. The nucleic acid segment may comprise deoxyribonucleic acids (i.e. DNA) or ribonucleic acids (i.e. RNA). The nucleic acid segment may further be single or double stranded. The nucleic acid segment may further be linear or circular in conformation. The nucleic acid segment may further comprise a promoter sequence functional in bacterial cells. The promoter may be inducible or constitutive. Promoters functional in bacterial cells are generally known to those of skill in the art, and include, but are not limited to the lac promoter, the bla promoter, the $P_L$ promoter, the $P_{trc}$ promoter, and the T7 promoter.

In an alternative embodiment, the invention provides a nucleic acid segment that encodes a polyhydroxyalkanoic acid synthase protein, and that encodes an acyl-CoA synthetase protein. The polyhydroxyalkanoic acid synthase protein may generally be any polyhydroxyalkanoic acid synthase protein suitable for the production of polyester materials according to the inventive processes. The polyhydroxyalkanoic acid synthase protein may be monomeric or dimeric. Monomeric polyhydroxyalkanoic acid synthase proteins include, but are not limited to, those from *Rhizobium meliloti, Alcaligenes eutrophus,* Alcaligenes sp., *Rhizobium etli, Paracoccus denitrificans,* Acinetobacter sp., *Rhodobacter sphaeroides, Methylobacterium extorquens, Pseudomonas oleovorans, Pseudomonas aeruginosa, Rhodococcus ruber,* and *Zoogloea ramigera.* Dimeric polyhydroxyalkanoic acid synthase proteins include, but are not limited to, those from *Thiocystis violacea* and *Chromatium vinosum.* Preferably, the polyhydroxyalkanoic acid synthase protein is an *Alcaligenes eutrophus* polyhydroxyalkanoic acid synthase protein, and more preferably, the *Alcaligenes eutrophus* polyhydroxyalkanoic acid synthase protein encoded by the *Alcaligenes eutrophus phaC* polyhydroxyalkanoic acid synthase structural gene. The acyl-CoA synthetase protein may be any acyl-CoA synthetase protein suitable for the preparation of polyester materials according to the inventive processes. Sources of acyl-CoA synthetase proteins include, but are not limited to, *Alcaligenes eutrophus, Methanothrix soehngenii,* and *Aspergillus nidulans.* Preferably, the acyl-CoA synthetase protein is a thiokinase protein, and more preferably, a 4-hydroxybutyrate thiokinase protein. The nucleic acid segment may comprise deoxyribonucleic acids (i.e. DNA) or ribonucleic acids (i.e. RNA). The nucleic acid segment may further be single or double stranded. The nucleic acid segment may further be linear or circular in conformation. The nucleic acid segment may further comprise a promoter sequence functional in bacterial cells. The promoter may be inducible or constitutive. Promoters functional in bacterial cells are generally known to those of skill in the art, and include, but are not limited to the lac promoter, the bla promoter, the $P_L$ promoter, the $P_{trc}$ promoter, and the T7 promoter.

The invention further provides recombinant vectors comprising a nucleic acid segment, wherein the segment encodes a polyhydroxyalkanoic acid synthase protein and encodes a fatty acid:acyl-CoA transferase protein. This vector may generally be any vector suitable for the delivery of the nucleic acid into a cell. Vectors are well known to those of skill in the art, and include, but are not limited to, plasmids, artificial chromosomes, viruses, bacteriophage, cosmids, and phagemids. In a preferred embodiment, the vector may be pKSSE5.3 or pSKSE5.3 as disclosed herein.

In a preferred embodiment, the invention encompasses a cell comprising a nucleic acid segment encoding a polyhydroxyalkanoic acid synthase protein and encoding a fatty acid:acyl-CoA transferase protein. The polyhydroxyalkanoic acid synthase protein may generally be any polyhydroxyalkanoic acid synthase protein suitable for the production of polyester materials according to the inventive processes. The polyhydroxyalkanoic acid synthase protein may be monomeric or dimeric. Monomeric polyhydroxyalkanoic acid synthase proteins include, but are not limited to, those from *Rhizobium meliloti, Alcaligenes eutrophus,* Alcaligenes sp., *Rhizobium etli, Paracoccus denitrificans,* Acinetobacter sp., *Rhodobacter sphaeroides, Methylobacterium extorquens, Pseudomonas oleovorans, Pseudomonas aeruginosa, Rhodococcus ruber,* and *Zoogloea ramigera.* Dimeric polyhydroxyalkanoic acid synthase proteins include, but are not limited to, those from *Thiocystis violacea* and *Chromatium vinosum.* Preferably, the polyhydroxyalkanoic acid synthase protein is an *Alcaligenes eutrophus* polyhydroxyalkanoic acid synthase protein, and more preferably, the *Alcaligenes eutrophus* polyhydroxyalkanoic acid synthase protein encoded by the *Alcaligenes eutrophus phaC* polyhydroxyalkanoic acid synthase structural gene. The fatty acid:acyl-CoA transferase protein may be any fatty acid:acyl-CoA transferase protein suitable for the preparation of polyester materials according to the inventive processes. Fatty acid:acyl-CoA transferase proteins include, but are not limited to, 4-hydroxybutyrate:acyl-CoA transferase from *Clostridium aminobutyricum,* propionate:acyl-CoA transferase from *Clostridium propionicum,* and succinate:acyl-CoA transferase from *Clostridium kluyveri.* Preferably, the fatty acid:acyl-CoA transferase protein is a 4-hydroxybutyrate:acyl-CoA transferase protein, more preferably a *Clostridium kluyveri* 4-hydroxybutyrate:acyl-CoA transferase protein, and most preferably, the *Clostridium kluyveri* 4-hydroxybutyrate:acyl-CoA transferase protein encoded by the *Clostridium kluyveri orfZ* 4-hydroxybutyrate:acyl-CoA transferase structural gene. The cell may generally be any cell suitable for the preparation of polyester materials. The cell may be, but is not limited to, a plant cell, a mammalian cells, an insect cell, a fungal cell, and a bacterial cell. Preferably, the cell is a plant cell. Preferably, the bacterial cell is *Escherichia coli,* and more preferably, the bacterial cell is *Escherichia coli* strain XL1-Blue.

In an alternative embodiment, the invention encompasses a cell comprising a nucleic acid segment encoding a polyhydroxyalkanoic acid synthase protein and encoding an acyl-CoA synthetase protein. The polyhydroxyalkanoic acid synthase protein may generally be any polyhydroxyalkanoic acid synthase protein suitable for the production of polyester materials according to the inventive processes. The polyhydroxyalkanoic acid synthase protein may be monomeric or dimeric. Monomeric polyhydroxyalkanoic acid synthase proteins include, but are not limited to, those from *Rhizobium meliloti, Alcaligenes eutrophus,* Alcaligenes sp., *Rhizobium etli, Paracoccus denitrificans,* Acinetobacter sp., *Rhodobacter sphaeroides, Methylobacterium extorquens, Pseudomonas oleovorans, Pseudomonas aeruginosa, Rhodococcus ruber,* and *Zoogloea ramigera.* Dimeric polyhydroxyalkanoic acid synthase proteins include, but are not limited to, those from *Thiocystis violacea* and *Chromatium vinosum.* Preferably, the polyhydroxyalkanoic acid synthase protein is an *Alcaligenes eutrophus* polyhydroxyalkanoic acid synthase protein, and more preferably, the *Alcaligenes eutrophus* polyhydroxyalkanoic acid synthase protein encoded by the *Alcaligenes eutrophus phaC* polyhydroxyalkanoic acid synthase structural gene. The acyl-CoA synthetase protein may be any acyl-CoA synthetase protein suitable for the preparation of polyester materials according to the inventive processes. Sources of acyl-CoA synthetase proteins include, but are not limited to, *Alcaligenes eutrophus, Methanothrix soehngenii,* and *Aspergillus nidulans.* Preferably, the acyl-CoA synthetase protein is a thiokinase protein, and more preferably a 4-hydroxybutyrate thiokinase protein. The cell may generally be any cell suitable for the preparation of polyester materials. The cell may be, but is not limited to, a plant cell, a mammalian cells, an insect cell, a fungal cell, and a bacterial cell. Preferably, the cell is a plant cell. Preferably, the bacterial cell is *Escherichia coli,* and more preferably, the bacterial cell is *Escherichia coli* strain XL1-Blue.

The invention further discloses methods for the preparation of a transformed cell, the transformed cell being suitable for the preparation of polyester materials. The type of cell includes, but is not limited to, a plant cell, a mammalian cell, an insect cell, a fungal cell, and a bacterial cell. Preferably, the cell is a plant cell. Alternatively, the cell is preferably a bacterial cell, more preferably the bacterial cell is *Escherichia coli,* and most preferably, the bacterial cell is *Escherichia coli* strain XL1-Blue. Means for the transformation of plants are well known in the art. Methods include, but are not limited to, liposome mediated transformation, electroporation, treatment with chemicals that increase free DNA uptake, free DNA delivery via microparticle bombardment, and transformation using viruses or pollen. Means for the transformation of bacterial cells are also well known in the art. Methods include, but are not limited to, electroporation, calcium chloride mediated transformation, and polyethylene glycol mediated transformation. The disclosed transformation methods comprise selecting a host cell, contacting the host cell with a nucleic acid segment encoding a polyhydroxyalkanoic acid synthase protein and encoding a fatty acid:acyl-CoA transferase protein, the contacting step being performed under conditions suitable for uptake of the nucleic acid segment by the cell. Subsequent regeneration of the cell affords the transformed cell. The polyhydroxyalkanoic acid synthase protein may generally be any polyhydroxyalkanoic acid synthase protein suitable for the production of polyester materials according to the inventive processes. The polyhydroxyalkanoic acid synthase protein may be monomeric or dimeric. Monomeric polyhydroxyalkanoic acid synthase proteins include, but are not limited to, those from *Rhizobium meliloti, Alcaligenes eutrophus,* Alcaligenes sp., *Rhizobium etli, Paracoccus denitrificans,* Acinetobacter sp., *Rhodobacter sphaeroides, Methylobacterium extorquens, Pseudomonas oleovorans, Pseudomonas aeruginosa, Rhodococcus ruber,* and *Zoogloea ramigera.* Dimeric polyhydroxyalkanoic acid synthase proteins include, but are not limited to, those from *Thiocystis violacea* and *Chromatium vinosum.* Preferably, the polyhydroxyalkanoic acid synthase protein is an *Alcaligenes eutrophus* polyhydroxyalkanoic acid synthase protein, and more preferably, the *Alcaligenes eutrophus* polyhydroxyalkanoic acid synthase protein encoded by the *Alcaligenes eutrophus phaC* polyhydroxyalkanoic acid synthase structural gene. The fatty acid:acyl-CoA transferase protein may be any fatty acid:acyl-CoA transferase protein suitable for the preparation of polyester materials according to the inventive processes. Fatty acid:acyl-CoA transferase proteins include, but are not limited to, 4-hydroxybutyrate:acetyl-CoA acyltransferase from *Clostridium aminobutyricum,* propionate:acetyl-CoA acyltransferase from *Clostridium propionicum,* and succinate:acetyl-CoA transferase from *Clostridium kluyveri.*

Preferably, the fatty acid:acyl-CoA transferase protein is a 4-hydroxybutyrate:acyl-CoA transferase protein, more preferably a *Clostridium kluyveri* 4-hydroxybutyrate:acyl-CoA transferase protein, and most preferably, the *Clostridium kluyveri* 4-hydroxybutyrate:acyl-CoA transferase protein encoded by the *Clostridium kluyveri orfZ* 4-hydroxybutyrate:acyl-CoA transferase structural gene.

The invention discloses alternative methods for the preparation of a transformed cell, the transformed cell being suitable for the preparation of polyester materials. The disclosed transformation methods comprise selecting a host cell, contacting the host cell with a nucleic acid segment encoding a polyhydroxyalkanoic acid synthase protein and encoding an acyl-CoA synthetase protein, the contacting step being performed under conditions suitable for uptake of the nucleic acid segment by the cell. Subsequent regeneration of the cell affords the transformed cell. The type of cell includes, but is not limited to, a plant cell, a mammalian cell, an insect cell, a fungal cell, and a bacterial cell. Preferably, the cell is a plant cell. Alternatively, the cell is preferably a bacterial cell, more preferably the bacterial cell is *Escherichia coli*, and most preferably, the bacterial cell is *Escherichia coli* strain XL1-Blue. Means for the transformation of plants are well known in the art. Methods include, but are not limited to, liposome mediated transformation, electroporation, treatment with chemicals that increase free DNA uptake, free DNA delivery via microparticle bombardment, and transformation using viruses or pollen. Means for the transformation of bacterial cells are also well known in the art. Methods include, but are not limited to, electroporation, calcium chloride mediated transformation, and polyethylene glycol mediated transformation. The polyhydroxyalkanoic acid synthase protein may generally be any polyhydroxyalkanoic acid synthase protein suitable for the production of polyester materials according to the inventive processes. The polyhydroxyalkanoic acid synthase protein may be monomeric or dimeric. Monomeric polyhydroxyalkanoic acid synthase proteins include, but are not limited to, those from *Rhizobium meliloti, Alcaligenes eutrophus,* Alcaligenes sp., *Rhizobium etli, Paracoccus denitrificans,* Acinetobacter sp., *Rhodobacter sphaeroides, Methylobacterium extorquens, Pseudomonas oleovorans, Pseudomonas aeruginosa, Rhodococcus ruber,* and *Zoogloea ramigera.* Dimeric polyhydroxyalkanoic acid synthase proteins include, but are not limited to, those from *Thiocystis violacea* and *Chromatium vinosum.* Preferably, the polyhydroxyalkanoic acid synthase protein is an *Alcaligenes eutrophus* polyhydroxyalkanoic acid synthase protein, and more preferably, the *Alcaligenes eutrophus* polyhydroxyalkanoic acid synthase protein encoded by the *Alcaligenes eutrophus phaC* polyhydroxyalkanoic acid synthase structural gene. The acyl-CoA synthetase protein may be any acyl-CoA synthetase protein suitable for the preparation of polyester materials according to the inventive processes. Sources of acyl-CoA synthetase proteins include, but are not limited to, *Alcaligenes eutrophus, Methanothrix soehngenii,* and *Aspergillus nidulans.* Preferably, the acyl-CoA synthetase protein is a thiokinase protein, and more preferably, a 4-hydroxybutyrate thiokinase protein.

The invention discloses methods for the preparation of polyester materials. The polyester materials may be any polyester material obtained via the inventive processes. The polyester may be a homopolyester or a copolyester. Preferably, the homopolyester is poly(4-hydroxybutyric acid) or poly(3-hydroxybutyric acid). The copolyester is preferably poly(3-hydroxybutyric acid-co-4-hydroxybutyric acid). In a preferred embodiment, the method comprises the steps of a) obtaining a cell containing a nucleic acid segment, the nucleic acid segment encoding a polyhydroxyalkanoic acid synthase protein and encoding a fatty acid:acyl-CoA transferase protein; b) establishing a culture of the cell; c) culturing the cell under conditions suitable for the production of a polyester; and d) isolating the polyester from the cell. The polyhydroxyalkanoic acid synthase protein may generally be any polyhydroxyalkanoic acid synthase protein suitable for the production of polyester materials according to the inventive method. The polyhydroxyalkanoic acid synthase protein may be monomeric or dimeric. Monomeric polyhydroxyalkanoic acid synthase proteins include, but are not limited to, those from *Rhizobium meliloti, Alcaligenes eutrophus,* Alcaligenes sp., *Rhizobium etli, Paracoccus denitrificans,* Acinelobacter sp., *Rhodobacter sphaeroides, Methylobacterium extorquens, Pseudomonas oleovorans, Pseudomonas aeruginosa, Rhodococcus ruber,* and *Zoogloea ramigera.* Dimeric polyhydroxyalkanoic acid synthase proteins include, but are not limited to, those from *Thiocystis violacea* and *Chromatium vinosum.* Preferably, the polyhydroxyalkanoic acid synthase protein is an *Alcaligenes eutrophus* polyhydroxyalkanoic acid synthase protein, and more preferably, the *Alcaligenes eutrophus* polyhydroxyalkanoic acid synthase protein encoded by the *Alcaligenes eutrophus phaC* polyhydroxyalkanoic acid synthase structural gene. The fatty acid:acyl-CoA transferase protein may be any fatty acid:acyl-CoA transferase protein suitable for the preparation of polyester materials according to the inventive method. Sources of acyl-CoA synthetase proteins include, but are not limited to, *Alcaligenes eutrophus, Methanothrix soehngenii,* and *Aspergillus nidulans.* Preferably, the fatty acid:acyl-CoA transferase protein is a 4-hydroxybutyrate:acyl-CoA transferase protein, more preferably a *Clostridium kluyveri* 4-hydroxybutyrate:acyl-CoA transferase protein, and most preferably, the *Clostridium kluyveri* 4-hydroxybutyrate:acyl-CoA transferase protein encoded by the *Clostridium kluyveri orfZ* 4-hydroxybutyrate:acyl-CoA transferase structural gene. The culture may contain glucose or any material capable of conversion to glucose by the cell, as a carbon source. The culture may contain 4-hydroxybutyric acid, the sodium salt of 4-hydroxybutyric acid, γ-butyrolactone, 1,4-butanediol, 4-hydroxyvaleric acid, γ-valerolactone, 1,4-pentanediol, 3-hydroxybutyric acid, the sodium salt of 3-hydroxybutyric acid, a hydroxypropionic acid, a hydroxybutyric acid, a hydroxyvaleric acid, a hydroxycaproic acid, a hydroxyheptanoic acid, a hydroxyoctanoic acid, a hydroxydecanoic acid, γ-caprolactone, γ-heptanoloactone, γ-octanolactone, γ-decanolactone, or any material capable of conversion to 4-hydroxybutyric acid by the cell. The culture may contain molecular oxygen. Molecular oxygen may be present due to bubbling of oxygen gas, or an oxygen containing gas, such as air, through the culture. Alternatively, the molecular oxygen may be present due to agitation of the culture. The cell may contain an protein capable of hydrolyzing lactones to the corresponding hydroxyalkanoic acids. Such proteins may include, but are not limited to, the 1,4-lactonase proteins from rat and humans. To facilitate conversion of 2-oxoglutarate to polyester materials, the cell may further comprise a 2-oxoglutarate decarboxylase protein (for example, from *Leuconostoc oenos* or *Euglena gracilis*) and a 4-hydroxybutyrate dehydrogenase protein (for example, from *C. Kluyveri* or *A. eutrophus*). To facilitate conversion of succinate to polyester materials, the cell may further comprise a succinate:acetyl-CoA transferase protein (for example, from *C. kluyveri*), a succinate-semialdehyde dehydrogenase protein (for example, from *C. kluyveri*), and a 4-hydroxybutyrate dehydrogenase protein. To facilitate conversion of succinyl-CoA to polyester materials, the cell may further comprise a succinate-semialdehyde dehydrogenase protein, and a 4-hydroxybutyrate dehydrogenase protein. To facilitate conversion of propionyl-CoA to polyester materials, the cell may further comprise a 2-methylcitrate synthase protein (for example, from *Saccharomyces* cerevisiae), a 2-methylcitrate dehyratase protein (for example, from *Saccharomyces cerevisiae*), a 2-methylisocitrate dehydratase protein (for example, from *Saccharomyces cerevisiae*), a 2-methylisocitrate lyase protein (for example, from *Saccharomyces cerevisiae*), a succinate:acetyl-CoA transferase protein (for example, from *C. kluyveri*), a succinate-semialdehyde dehydrogenase protein, and a 4-hydroxybutyrate dehydrogenase protein. It will be apparent to those of skill in the art that different combinations of polyhydroxyalkanoic acid synthases, fatty acid:acyl-CoA transferases, and chemical substrates can be used according to the inventive methods to afford polyester materials.

The invention further describes alternative methods for the preparation of polyester materials. In a preferred embodiment, the method comprises the steps of a) obtaining a cell containing a nucleic acid segment, the nucleic acid segment encoding a polyhydroxyalkanoic acid synthase protein and encoding an acyl-CoA synthetase protein; b) establishing a culture of the cell; c) culturing the cell under conditions suitable for the production of a polyester; and d) isolating the polyester from the cell. The polyester materials may be any polyester material obtained via the inventive processes. The polyester may be a homopolyester or a copolyester. Preferably, the homopolyester is poly(4-hydroxybutyric acid) or poly(3-hydroxybutyric acid). The copolyester is preferably poly(3-hydroxybutyric acid-co-4-hydroxybutyric acid). The polyhydroxyalkanoic acid synthase protein may generally be any polyhydroxyalkanoic acid synthase protein suitable for the production of polyester materials according to the inventive method. The polyhydroxyalkanoic acid synthase protein may be monomeric or dimeric. Monomeric polyhydroxyalkanoic acid synthase proteins include, but are not limited to, those from *Rhizobium meliloti*, *Alcaligenes eutrophus*, *Alcaligenes sp.*, *Rhizobium etli*, *Paracoccus denitrificans*, *Acinetobacter sp.*, *Rhodobacter sphaeroides*, *Methylobacterium extorquens*, *Pseudomonas oleovorans*, *Pseudomonas aeruginosa*, *Rhodococcus ruber*, and *Zoogloea ramigera*. Dimeric polyhydroxyalkanoic acid synthase proteins include, but are not limited to, those from *Thiocystis violacea* and *Chromatium vinosum*. Preferably, the polyhydroxyalkanoic acid synthase protein is an *Alcaligenes eutrophus* polyhydroxyalkanoic acid synthase protein, and more preferably, the *Alcaligenes eutrophus* polyhydroxyalkanoic acid synthase protein encoded by the *Alcaligenes eutrophus* phaC polyhydroxyalkanoic acid synthase structural gene. The acyl-CoA synthetase protein may be any acyl-CoA synthetase protein suitable for the preparation of polyester materials according to the inventive processes. Sources of acyl-CoA synthetase proteins include, but are not limited to, *Alcaligenes eutrophus*, *Methanothrix soehngenii*, and *Aspergillus nidulans*. Preferably, the acyl-CoA synthetase protein is a thiokinase protein, and more preferably, a 4-hydroxybutyrate thiokinase protein. The culture may contain glucose or any material capable of conversion to glucose by the cell, as a carbon source. The culture may contain 4-hydroxybutyric acid, the sodium salt of 4-hydroxybutyric acid, γ-butyrolactone, 1,4-butanediol, 4-hydroxyvaleric acid, γ-valerolactone, 1,4-pentanediol, 3-hydroxybutyric acid, the sodium salt of 3-hydroxybutyric acid, a hydroxypropionic acid, a hydroxybutyric acid, a hydroxyvaleric acid, a hydroxycaproic acid, a hydroxyheptanoic acid, a hydroxyoctanoic acid, a hydroxydecanoic acid, γ-caprolactone, γ-heptanoloactone, γ-octanolactone, γ-decanolactone, or any material capable of conversion to 4-hydroxybutyric acid by the cell. The culture may contain molecular oxygen. Molecular oxygen may be present due to bubbling of oxygen gas, or an oxygen containing gas, such as air, through the culture. Alternatively, the molecular oxygen may be present due to agitation of the culture. The cell may contain an enzyme capable of hydrolyzing lactones to the corresponding hydroxyalkanoic acids. Such proteins may include, but are not limited to, the 1,4-lactonase proteins from rat and humans. To facilitate conversion of 2-oxoglutarate to polyester materials, the cell may further comprise a 2-oxoglutarate decarboxylase protein and a 4-hydroxybutyrate dehydrogenase protein. To facilitate conversion of succinate to polyester materials, the cell may further comprise a succinate:acetyl-CoA transferase protein, a succinate-semialdehyde dehydrogenase protein, and a 4-hydroxybutyrate dehydrogenase protein. To facilitate conversion of succinyl-CoA to polyester materials, the cell may further comprise a succinate-semialdehyde dehydrogenase protein, and a 4-hydroxybutyrate dehydrogenase protein. To facilitate conversion of propionyl-CoA to polyester materials, the cell may further comprise a 2-methylcitrate synthase protein, a 2-methylcitrate dehyratase protein, a 2-methylisocitrate dehydratase protein, a 2-methylisocitrate lyase protein, a succinate:acetyl-CoA transferase protein, a succinate-semialdehyde dehydrogenase protein, and a 4-hydroxybutyrate dehydrogenase protein. It will be apparent to those of skill in the art that different combinations of polyhydroxyalkanoic acid synthases, acyl-CoA synthetases, and chemical substrates can be used according to the inventive methods to afford polyester materials.

In a further alternative embodiment, the preparation of polyester materials may be achieved by the co-expression of a polyhydroxyalkanoic acid synthase protein, an acyl kinase protein, and a phosphotransacylase protein. A source of acyl kinase includes, but is not limited to, the butyrate kinase from *Clostridium acetobutylicum*. A source of a phosphotransacylase protein includes, but is not limited to, the phosphotransbutyrylase protein from *Clostridium acetobutylicum*.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Materials and Methods

Microbiological Deposit

A deposit according to the Budapest Treaty of *Escherichia coli* XL1-Blue containing the recombinant plasmid pKSSE5.3 (accession number DSM 11427) and of *Escherichia coli* XL1-Blue containing the recombinant plasmid pSKSE5.3 (accession number DSM 11435) was made on Feb. 24, 1997 with the Deutsche Sammlung von Mikroorganismen und Zellkulturen GmbH (DSMZ), Mascheroder Weg 1b, D-38124 Braunschweig, Germany.

Bacterial strains and plasmids

*Escherichia coli* strain XL1-Blue (Bullock, W. O. et al. (1987) *BioTechniques* 5:376–378) and the plasmids pBluescriptKS and pBluescriptSK (Stratagene, La Jolla, Calif.), pSK2665 (Schubert, P. et al. (1991) *J. Bacteriol.* 173:168–175) and pCK3pSK (Söhling, B. and Gottschalk, G. (1996) *J. Bacteriol.* 178:871–880) were used.

Media and cultivation conditions

Cells of *Escherichia coli* were cultivated at 37° C. in complex Luria-Bertani broth or in M9-minerals salts medium supplemented with 0.02% (w/vol) yeast extract (Sambrook, J. et al. (1989) Molecular cloning; a laboratory manual. 2nd edition. Cold Spring Harbor Laboratory, Cold Spring Harbor, N.Y.). The addition of antibiotics prepared according to Sambrook, J. et al. (1989), and of carbon sources, which were sterilized by filtration, are described in the text. Cultivations were performed either on solidified media, which were obtained by the addition of 1.5% (wt/vol) agar, or in liquid media in erlenmeyer flasks incubated on a rotary shaker.

Isolation and analysis of polyesters

For quantitative determination of polyhydroxyalkanoic acid and for the analysis of the constituents of polyhydroxyalkanoic acid, 3–5 mg of lyophilized cell material or the isolated polyester were subjected to methanolysis in the presence of 15% (vol/vol) sulfuric acid. The resulting hydroxyacyl methylesters were analyzed by gas chromatography as described in detail by Brandl, H. et al. (1988, *Appl. Environ. Microbiol.* 54:1977–1982) and Timm. A. et al. (1990, *Appl. Microbiol. Biotechnol.* 33:296–301).

Polyhydroxyalkanoic acids were isolated from lyophilized cells by extraction with chloroform in a soxhlet apparatus. The polyester was precipitated from the chloroform solution by the addition of 10 volumes of ethanol, and the precipitate was subsequently separated from the solvents by filtration. Remaining solvents were removed by exposure of the polyester to a stream of air. For further purification, the polyester was dissolved in chloroform and the precipitation with ethanol was repeated.

Nucleic acid techniques Plasmid DNA and DNA restriction fragments were isolated and analyzed by standard methods (Sambrook, J. et al. (1989) Molecular cloning; a laboratory manual. 2nd edition. Cold Spring Harbor Laboratory, Cold Spring Harbor, N.Y.). Restriction enzymes, ligases, and other enzymes were used according to the manufacturer's instructions.

Physical characterization of poly(4-hydroxybutyric acid) samples

Analysis of polymer composition was performed using gas chromatography methods as described by Braunegg, G. et al. (1978, *Eur. J. Appl. Microbiol.* 6:29–37). Analysis of molecular weight and polydispersity was performed by gel permeation chromatography (GPC, Ishihara, Y. et al. (1996) *J. Ferm. Bioeng.* 81:422–428). Analysis of melting points, rate of crystallization, $dH_m$, and $E_a$ were performed by differential scanning calorimetry (DSC, Kemnitzer, J. E. et al. (1995) *J. Env. Polym. Degrad.* 3:37–47).

EXAMPLE 1

Construction of plasmids

A 3.5-kbp SmaI/ApaI restriction fragment comprising the entire polyhydroxyalkanoic acid synthase structural gene (phaC$_{Ae}$, GenBank Accession number J05003, SEQ ID NO: 1, Peoples, O.P. and Sinskey, A.J. (1989) *J. Biol. Chem.* 264:15298–15303) plus 878 of 1,221 bp of the 5' region of the β-ketothiolase structural gene from *A. eutrophus*, referred to as SA35, was isolated from the hybrid plasmid pSK2665 that had been cloned previously (Schubert, P. et al. (1991) *J. Bacteriol.* 173:168–175). In addition, a 1.8 kb ApaI/EcoRI restriction fragment comprising the entire orfZ$_{Ck}$ (phaA'$_{Ae}$, GenBank Accession number L21902, SEQ ID NO: 2, Söhling, B. and Gottsvhalk, G. (1993) *J. Bacteriol.* 178:871–880) from *C. kluyveri*, and referred to as AE18, was isolated from the hybrid plasmid pCK3pSK that had been cloned previously (Söhling, B. and Gottschalk, G. (1996) *J. Bacteriol.* 178:871–880). Both fragments were ligated to EcoRI/SmaI digested pBluescript vectors KS⁻ and SK⁻. The ligation products (pKSSE5.3 and pSKSE5.3, respectively) were transformed into *Escherichia coli* strain XL1-Blue using calcium chloride methodologies (Sambrook, J. et al. (1989) Molecular cloning; a laboratory manual. 2nd edition. Cold Spring Harbor Laboratory, Cold Spring Harbor, N.Y.). Plasmid pKSSE5.3 contains phaC$_{Ae}$ and orfZ$_{Ck}$ adjacent but antilinear to the lacZ promoter. In pSKSE5.3, phaC$_{Ae}$ and orfZ$_{Ck}$ were located downstream and colinear to the lacZ promoter. All constructs were analyzed by agarose gel electrophoresis for the presence of the expected restriction fragments.

For control experiments, fragment SA35 was ligated to pBluescript KS⁻ or to pBluescript SK⁻ resulting in the plasmids pKSSA35 (phaC$_{Ae}$ plus phaA'$_{Ae}$ adjacent but antilinear to the lacZ promoter) or pSKSA35 (phaC$_{Ae}$ plus phaA'$_{Ae}$ downstream and colinear to the lacZ promoter), respectively. Similarly, fragment AE18 alone was ligated to pBluescript KS⁻ or to pBluescript SK⁻ resulting in the plasmids pKSAE18 (orfZ$_{Ck}$ downstream and colinear to the lacZ promoter) and pSKAE18 (orfZ$_{Ck}$ adjacent but antilinear to the lacZ promoter), respectively.

EXAMPLE 2

Synthesis of poly(4-hydroxybutyric acid) from 4-hydroxybutyric acid in recombinant strains of *Escherichia coli*

The recombinant strains of *Escherichia coli* XL1-Blue were cultivated at 37° C. as batch cultures in erlenmeyer flasks either using LB complex medium supplemented with 4-hydroxybutyric acid alone or in combination with glucose as an additional carbon source, or M9 mineral salts medium containing 4-hydroxybutyric acid and glucose as carbon sources. The hybrid plasmids pKSSE5.3 and pSKSE5.3, which comprised phaC$_{Ae}$, phaA'$_{Ae}$ plus orfZ$_{Ck}$, conferred to *Escherichia coli* the capability to synthesize and accumulate a homopolyester of 4-hydroxybutyric acid if the strains were cultivated in the presence of 4-hydroxybutyric acid plus glucose as carbon source (Table 1).

TABLE 1

Accumulation of poly(4-hydroxybutyric acid) by recombinant strains of *Escherichia coli* XL1-Blue from 4-hydroxybutyric acid plus glucose

| Medium | Carbon source | volume of medium (mL) | PHA content (% of CDW) | accumulated polyester |
|---|---|---|---|---|
| with pSKSE5.3 | | | | |
| LB + IPTG | 0.5% glucose 0.4% 4HB (sodium salt) | 50 | 3.3 | poly (4HB) |
| LB + IPTG | 0.5% glucose 0.4% 4HB (sodium salt) | 100 | 10.5 | poly (4HB) |
| LB + IPTG | 0.5% glucose 0.4% 4HB (sodium salt) | 150 | 8.8 | poly (4HB) |

TABLE 1-continued

Accumulation of poly(4-hydroxybutyric acid) by recombinant strains of *Escherichia coli* XL1-Blue from 4-hydroxybutyric acid plus glucose

| Medium | Carbon source | volume of medium (mL) | PHA content (% of CDW) | accumulated polyester |
|---|---|---|---|---|
| M9 + IPTG with pKSSE5.3 | 0.5% glucose 0.4% 4HB (sodium salt) | 100 | 16.9 | poly (4HB) |
| LB | 0.5% glucose 0.4% 4HB (sodium salt) | 50 | 4.3 | poly (4HB) |
| LB | 0.5% glucose 0.4% 4HB (sodium salt) | 100 | 40.8 | poly (4HB) |
| LB | 0.5% glucose 0.4% 4HB (sodium salt) | 150 | 20.4 | poly (4HB) |
| M9 with pSKSA35 | 0.5% glucose 0.4% 4HB (sodium salt) | 100 | 58.5 | poly (4HB) |
| LB + IPTG | 0.5% glucose 0.4% 4HB (sodium salt) | 50–150 | nd | — |
| M9 + IPTG with pKSAE18 | 0.5% glucose 0.4% 4HB (sodium salt) | 100 | nd | — |
| LB + IPTG | 0.5% glucose 0.4% 4HB (sodium salt) | 50–150 | nd | — |
| M9 + IPTG | 0.5% glucose 0.4% 4HB (sodium salt) | 100 | nd | — |

Cells were cultivated at 37° C. for 72 hours in one-stage cultivation experiments in 250 mL erlenmeyer flasks as described in the text that were incubated on a rotary shaker (220 rpm). The cultures were inoculated with 0.04 vol of an overnight preculture in Luria Bertani broth containing 0.5% (wt/vol) glucose plus 0.4% (wt/vol) 4-hydroxybutyric acid. M9 medium was supplemented with 0.02% (wt/vol) yeast extract. At the end of the experiment, the cells were harvested, washed with tap water, lyophilized and analyzed for PHA content and composition by gas chromatography.
Abbreviations and symbols: IPTG, isopropyl-1-thio-β-D-galactopyranoside; nd, not detectable; —, not relevant.

Light microscopic examination of the cells revealed cytoplasmic inclusions, and the harvested cells were more opaque in appearance than were strains not harboring pKSSE5.3 or pSKSE5.3. If glucose was omitted as a cosubstrate, the amount of polyhydroxyalkanoic acid in the cells was approximately in the same range but consisting of a copolyester of 3-hydroxybutyric acid and 4-hydroxybutyric acid, poly(3-hydroxybutyric acid-co-4-hydroxybutyric acid), rather than poly(4-hydroxybutyric acid). Early in the growth, only 4-hydroxybutyric acid was incorporated into the polyhydroxyalkanoic acid. However, after approximately one day of cultivation, the cells began to incorporate increasing amounts of 3-hydroxybutyric acid, and after four days, the molar fraction of 3-hydroxybutyric acid had increased to approximately 70% (Table 2). If glucose was provided as the sole carbon source, no polyhydroxyalkanoic acid was accumulated. The addition of 4-hydroxybutyric acid to the medium as a carbon source appeared essential to obtain poly(4-hydroxybutyric acid), and glucose provided as a cosubstrate appeared to limit the incorporation of 3-hydroxybutyric acid into the polyhydroxyalkanoic acid.

TABLE 2

Accumulation of poly (3-hydroxybutyric acid-co-4-hydroxybutyric acid) by recombinant strains of *Escherichia coli* XL1-Blue from 4-hydroxybutyric acid

| Strain and Carbon source(s) | Incubation time (hours) | PHA content (% of CDW) | PHA composition mole % 3HB | PHA composition mole % 4HB |
|---|---|---|---|---|
| *E. coli* XL1-Blue (pSKSE5.3) | | | | |
| in LB medium with 0.5% glucose and 0.4% Na-4-hydroxybutyrate | 20 | 13.3 | nd | 100 |
| | 44 | 13.1 | 11 | 89 |
| | 72 | 11.1 | 55 | 45 |
| | 94 | 15.1 | 64 | 36 |
| in LB medium with 0.4% Na-4-hydroxybutyrate | 20 | 20.2 | nd | 100 |
| | 44 | 20.6 | 72 | 28 |
| | 72 | 10.2 | 61 | 39 |
| | 94 | 21.9 | 66 | 34 |

TABLE 2-continued

Accumulation of poly (3-hydroxybutyric acid-co-4-hydroxybutyric acid) by recombinant strains of *Escherichia coli* XL1-Blue from 4-hydroxybutyric acid

| Strain and Carbon source(s) | Incubation time (hours) | PHA content (% of CDW) | PHA composition mole % 3HB | PHA composition mole % 4HB |
|---|---|---|---|---|
| *E. coli* XL1-Blue (pKSSE5.3) | | | | |
| in LB medium with | 20 | 14.6 | nd | 100 |
| 0.5% glucose and | 44 | 13.6 | nd | 100 |
| 0.4% Na-4-hydroxybutyrate | 72 | 7.0 | nd | 100 |
| | 94 | 15.9 | 7 | 93 |
| in LB medium with | 20 | 22.9 | nd | 100 |
| 0.4% Na-4-hydroxybutyrate | 44 | 21.4 | 62 | 38 |
| | 72 | 23.7 | 63 | 37 |
| | 94 | 29.8 | 64 | 36 |

Cells were cultivated at 37° C. in 50 mL Luria Bertani complex medium, which contained the indicated carbon source, in 300 mL Erlenmeyer flasks. At the indicated times, 10 mL samples were withdrawn and subjected to gas chromatographic analysis of the polyester content and composition.
Abbreviations and symbols: nd, not detectable; PHA, polyhydroxyalkanoic acids; 3HB, 3-hydroxybutyric acid; 4HB, 4-hydroxybutyric acid; LB Luria Bertani; CDW, cellular dry weight Gas chromatographic analysis of the derivatives obtained from washed and lyophilized whole cells gave two major compounds in the chromatograms exhibiting retention times of 20.1 and 9.3 and one minor compound exhibiting a retention time of 24.1 min. These compounds represented most probably γ-butyrolactone, the methylester of 4-hydroxybutyric acid and the methyl ether of 4-hydroxybutyric acid, respectively, that were also obtained if only 4-hydroxybutyric acid were subjected to acidic methanolysis.

The amount of poly(4-hydroxybutyric acid) accumulated by the cells depended upon the plasmid present in the recombinant *Escherichia coli* XL1-Blue, the medium, and the cultivation conditions. Recombinant strains harboring plasmid pKSSE5.3 accumulated significantly more poly(4-hydroxybutyric acid) as compared to those harboring pSKSE5.3 in LB complex medium as well as in M9 mineral salts medium (Table 1). The addition of IPTG to cultures of *Escherichia coli* XL1-Blue harboring pSKSE5.3 did not significantly influence the amount of polyester produced. With either plasmid, the amount of poly(4-hydroxybutyric acid) accumulated by the cells was always higher in M9-mineral salts medium than in LB complex medium. Supplementation of oxygen to the cultures seems to be crucial for the amount of poly(4-hydroxybutyric acid) accumulated by the cells. This became obvious from experiments in which the ratio of the medium volume to the volume of the erlenmeyer flask was varied. When experiments were performed in a 250 mL erlenmeyer flask, the amount of poly(4-hydroxybutyric acid) increased tremendously when the volume of the medium was increased from 50 to 100 mL independently whether the recombinant strains harbored pSKSE5.3 or pKSSE5.3 (Table 1). If the volume of the medium was further increased to 150 mL, the amount of accumulated poly(4-hydroxybutyric acid) decreased.

All plasmids, which contained only phaC$_{Ae}$ plus phaA'$_{Ae}$ (pKSSA35 and pSKSA35) or only orfZ$_{Ck}$ (pKSAE18 and pSKAE18), did not confer to *Escherichia coli* the capability to synthesize detectable poly(4-hydroxybutyric acid) or of any other polyhydroxyalkanoic acid if 4-hydroxybutyric acid or glucose alone or in combination were used a carbon sources and independent from the volume of the medium or whether IPTG was added or not.

None of the recombinant strains of *Escherichia coli* obtained in this study were able to grow in liquid or on solidified M9 minerals salts medium containing 4-hydroxybutyric acid as the sole carbon source.

EXAMPLE 3

Properties of poly(4-hydroxybutyric acid) isolated from recombinant *Escherichia coli*

In order to confirm accumulation of poly(4-hydroxybutyric acid) by the recombinant strains and to isolate the polyester from the cells, *Escherichia coli* XL1-Blue (pKSSE5.3) was cultivated in M9 mineral salts medium on a larger scale. 2 L baffled erlenmeyer flasks containing 1700 mL medium supplemented with 0.4% (wt/vol) sodium 4-hydroxybutyrate and 1% or 2% glucose were inoculated with a preculture of 50 mL cells and incubated on a rotary shaker for 72 hours. This afforded approximately 1.9 g or 2.5 g, respectively, of dried cells. Gas chromatographic analysis of the whole cells indicated a poly(4-hydroxybutyric acid) content of approximately 80% (wt/wt). From these cells, 0.8 g or 1.1 g of polyhydroxyalkanoic acid could be extracted with chloroform and precipitated with ethanol, respectively. Therefore, only 52% or 55% of the polyester were recovered from the cells. This discrepancy could be explained by incomplete extractions of the cells since the extracted cells still contained poly(4-hydroxybutyric acid) and by losses during the precipitation of the polymer. The isolated material gave in the gas chromatogram only those signals indicative of 4-hydroxybutyric acid. Thus it was confirmed that the cells had accumulated poly(4-hydroxybutyric acid) homopolyester.

Poly(4-hydroxybutyric acid) produced by a polyhydroxyalkanoic acid-leaky mutant of *A. eutrophus* JMP222 and recombinant strains of this mutant harboring extra copies of the *A. eutrophus* PHA synthase operon (Steinbüchel, A. et al. (1994) *J. Environ. Polymer Degrad.* 2:67–74) were observed to be extracted from lyophilized cells at a lower rate than was poly(3-hydroxybutyric acid). Similarly, the poly(4-hydroxybutyric acid) produced by the recombinant strain of Escherichia coli employed in this study was extracted from lyophilized cells at a much lower rate than, for example poly(3-hydroxybutyric acid). Poly(4-hydroxybutyric acid) from the recombinant strain precipitated in the presence of an excess of ethanol from the chloroform solution as a highly fibrous material which easily and almost quantitatively ended up on a glass rod if the latter was used for stirring during precipitation. Poly(4-hydroxybutyric acid) from the strains of A. eutrophus JMP222 (Steinbüchel, A. et al. (1994) J. Environ. Polymer Degrad. 2:67–74) was isolated as a white and elastic material.

Gel permeation chromatography experiments performed with two samples of poly(4-hydroxybutyric acid) homopolyester isolated from two independent batches of cells of recombinant strains of E. coli revealed molecular weights ($M_w$) of $1.75 \times 10^6$ and $1.85 \times 10^6$, respectively, with relative low polydispersities ($M_w/M_n$) of 1.45 and 1.48, respectively. Therefore, the molecular weights of these poly (4-hydroxybutyric acid) samples were significantly higher than the molecular weights of poly(4-hydroxybutyric acid) isolated from strains of A. eutrophus JMP222. In addition, the polydispersity of these samples was much lower (Steinbüchel, A. et al. (1994) J. Environ. Polymer Degrad. 2:67–74). The two poly(4-hydroxybutyric acid) samples exhibited melting points ($T_m$) of 67.6 and 63.1° C. The values for $dH_m$ and $E_a$ for the two samples were 45.7 and 44.3 J/g or 69.8 and 83.8 KJ/mol, respectively. At 70° C. both polyester samples exhibited a slow rate for crystallization (>30 min).

EXAMPLE 4

Synthesis of polyhydroxyalkanoic acid from γ-butyrolactone, levulinic acid, 4-hydroxyvaleric acid or γ-valerolactone in recombinant strains of Escherichia coli Carbon sources related to 4-hydroxybutyric acid were also investigated with respect to the formation of polyhydroxyalkanoic acid by the recombinant strains. For this purpose, cells were cultivated in two different stages. In the first stage the cells were grown for 64 hours in the complete M9 minerals salts medium containing 0.5% (wt/vol) glucose plus 0.1% (wt/vol) sodium 4-hydroxybutyrate as carbon sources. These cells were then washed with fresh M9 mineral salts medium and transferred to 250 mL erlenmeyer flasks containing 100 mL ammonium-free M9 mineral salts medium. The density of the cell suspension was diluted approximately 1:1 as compared to the density in the preculture. In the second stage the cells were cultivated for 72 hours on a rotary shaker. If Escherichia coli XL1-Blue (pKSSE5.3) was cultivated in M9 mineral salts medium containing 0.5% (wt/vol) glucose plus 0.4% (wt/vol) γ-butyrolactone as carbon sources, only low amounts of polyhydroxyalkanoic acid (usually below 10% of CDW, wt/wt) were accumulated (Table 3). However, these cells did not accumulate poly(4-hydroxybutyric acid) homopolyester but synthesized a copolyester consisting of 3-hydroxybutyric acid and 4-hydroxybutyric acid, with 4-hydroxybutyric acid as a minor constituent (usually below 30%, mol/mol).

TABLE 3

Cultivation of E. coli XL1-Blue (pKSSE5.3) on other precursor substrates for the incorporation of 4-hydroxyalkanoic acids in PHA

| Medium | Carbon source | PHA content (% of CDW) | PHA composition (mole %) | | | |
|---|---|---|---|---|---|---|
| | | | 3HB | 3HV | 4HB | 4HV |
| two-stage cultivation experiments | | | | | | |
| M9* | 0.5% glucose 0.4% γ-butyrolactone | 9.6 | 71 | nd | 29 | nd |
| M9* | 0.5% glucose 0.4% Na-levulinate | 4.2 | 100 | nd | nd | nd |
| M9* | 0.5% glucose 0.4% Na-4-hydroxyvalerate | 1.5 | 100 | nd | nd | nd |
| M9* | 0.5% glucose 0.4% γ-valerolactone | 2.7 | 100 | nd | nd | nd |
| one-stage cultivation experiments | | | | | | |
| M9 | 0.5% glucose 0.1% γ-butyrolactone | 8.0 | nd | nd | 100 | nd |
| M9 | 0.5% glucose 0.2% γ-butyrolactone | 13.9 | nd | nd | 100 | nd |
| M9 | 0.5% glucose 0.4% γ-butyrolactone | 16.1 | nd | nd | 100 | nd |
| M9 | 0.5% glucose 0.2% Na-levulinate | nd | nd | nd | nd | nd |
| M9 | 0.5% glucose 0.4% Na-levulinate | nd | nd | nd | nd | nd |

Cells were cultivated at 37° C. for 72 hours in one- or two-stage cultivation experiments as described in the text. At the end of the experiment the cells were harvested, washed with tap water, lyophilized and analyzed for PHA content and composition by gas chromatography.
Abbreviations and symbols: M9, regular mineral salts medium supplemented with 0.02% (wt/vol) yeast extract; M9*, ammonium-free M9 mineral salts medium; nd, not detectable If in these experiments γ-butyrolactone was replaced by 0.4% (wt/vol) sodium levulinate or by 0.2% (wt/vol) sodium 4-hydroxyvalerate or by 0.2% (wt/vol) γ-valerolactone, only very low amounts of polyhydroxyalkanoic acid never exceeding 4% of the CDW were synthesized and accumulated. Gas chromatographic analysis revealed 3-hydroxybutyric acid as the only constituent; 4-hydroxybutyric acid, 3-hydroxyvaleric acid (3HV) or 4-hydroxyvaleric acid (4HV) were not detected (Table 3).

Cells of Escherichia coli XL1-Blue (pKSSE5.3) were also cultivated in single stage experiments as batch cultures in 250 mL erlenmeyer flasks containing 100 mL complete M9 minerals salts medium plus 0.5%/wt/vol) glucose plus 0.1 to 0.4% (wt/vol) γ-butyrolactone as carbon sources. The cells accumulated significantly more polyhydroxyalkanoic acid, and the polyester consisted of 4-hydroxybutyric acid as the only detectable constituent (Table 3). With 0.4% (wt/vol) sodium 4-hydroxybutyrate in the medium, for example, poly(4-hydroxybutyric acid) contributed 16.1% (wt/wt) to the CDW. If sodium levulinate instead of sodium 4-hydroxybutyrate was used as a second carbon source in addition to 0.5% (wt/vol) glucose, no polyhydroxyalkanoic acid was detected in the cells.

EXAMPLE 5

Production of polyester materials in plants

In plants, transformation vectors capable of introducing bacterial genes involved in polyester biosynthesis can be designed. Generally, such vectors comprise one or more coding sequences of interest under the transcriptional control of 5' and 3' regulatory sequences, including a promoter, and a selectable marker. Typical regulatory sequences include a transcription initiation start site, an RNA processing signal, a transcription termination site, and/or a polyadenylation signal. Plant promoter can be inducible or constitutive, environmentally- or developmentally-regulated, or cell- or tissue-specific. Often-used promoters include the CaMV 35S promoter (Odell, J. T. et al. (1985) *Nature* 313:810–812), the enhanced CaMV 35S promoter, the Figwort Mosaic Virus (FMV) promoter (Richins, R. D. et al. (1987) *NAR* 20:8451–8466), the mannopine synthase (mas) promoter, the nopaline synthase (nos) promoter, and the octopine synthase (ocs) promoter. Useful inducible promoters include heat-shock promoters (Ou-Lee et al. (1986) *Proc. Natl. Acad. Sci. USA* 83:6815; a nitrate-inducible promoter derived from the spinach nitrite reductase gene (Back, E. et al. (1991) *Plant Mol. Biol.* 17:9–18); hormone-inducible promoters (Yamaguchi-, K. et al. (1990) *Plant Mol. Biol.* 15:905–912; Kares, C. et al. (1990) *Plant Mol. Biol.* 15:225–236), and light-inducible promoters associated with the small subunit of RuBP carboxylase and LHCP gene families (Kuhlemeier, C. et al. (1989) *Plant Cell* 1:471–478; Feinbaum, R. L. et al. (1991) *Mol. Gen. Genet.* 226:449–456; Weisshaar, B. et al. (1991) *EMBO J.* 10:1777–1786; Lam, E. and Chua, N.-H. (1990) *Science* 248:471–474; Castresana, C. et al. (1988) *EMBO J.* 7:1929–1936; Schulze-Lefert, P. et al. (1989) *EMBO J.* 8:651–656). Examples of useful tissue-specific, developmentally-regulated promoters include the β-conglycinin 7S promoter (Doyle, J. J. et al. (1986) *J. Biol. Chem.* 261:9228–9238; Slighton and Beachy (1987) *Planta* 172:356), and seed-specific promoters (Knutzon, D. S. et al. (1992) *Proc. Natl. Acad. Sci. USA* 89:2624–2628; Bustos, M. M. et al. (1991) *EMBO J.* 10:1469–1480; Lam, E. and Chua, N.-H. (1991) *Science* 248:471–474; Stayton, M. et al. (1991) *Aust. J. Plant. Physiol.* 18:507–518). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al. (1991) *Seed Sci. Res.* 1:209), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Hoffman, U.S. Pat. No. 5,106,739), or to combine desired transcriptional activity and tissue specificity. Representative vectors often comprise, operatively linked in sequence in the 5' to 3' direction, a promoter sequence that directs the transcription of a downstream heterologous structural nucleic acid in a plant; optionally, a non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding said protein. Additionally, a factor to consider is the timing and intracellular localization of proteins necessary for the biosynthesis of polyesters. For example, if fatty acid biosynthetic pathways are utilized in oilseed plants such as canola, then polyester biosynthetic protein expression should be concurrent with fatty acid biosynthesis and targeted to the seed leucoplast or leaf chloroplast.

A variety of different methods can be employed to introduce such vectors into plant protoplasts, cells, callus tissue, leaf discs, meristems, etcetera, to generate transgenic plants, including Agrobacterium-mediated transformation, particle gun delivery, microinjection, electroporation, polyethylene glycol-mediated protoplast transformation, liposome-mediated transformation, etcetera (reviewed in Potrykus, I. (1991) *Annu. Rev. Plant Physiol. Plant Mol. Biol.* 42:205–226). In general, transgenic plants comprising cells containing and expressing polyhydroxyalkanoic acid synthase and fatty acid:acyl-CoA transferase-encoding nucleic acid can be produced by transforming plant cells with a nucleic acid construct as described above via any of the foregoing methods; selecting plant cells that have been transformed on a selective medium; regenerating plant cells that have been transformed to produce differentiated plants; and selecting a transformed plant which expresses the polyhydroxyalkanoic acid synthase and fatty acid:acyl-CoA transferase-encoding nucleotide sequences.

The encoding nucleic acids can be introduced either in a single transformation event (all necessary DNAs present on the same vector), a co-transformation event (all necessary nucleic acids present on separate vectors that are introduced into plants or plant cells simultaneously), by independent transformation events (all necessary nucleic acids present on separate vectors that are introduced into plants or plant cells independently) or by re-transformation (transforming an already transformed line generated by a single transformation, co-transformation, or independent transformation events). Traditional breeding methods, when applicable, can subsequently be used to incorporate the entire pathway into a single plant. Successful production of the PHA polyhydroxybutyrate in cells of Arabidopsis has been demonstrated by Poirier, Y. et al. (1992, *Science* 256:520–523), and in plastids thereof by Nawrath et al. (1994, *Proc. Natl. Acad. Sci. USA* 91:12760–12764).

Specific methods for transforming a wide variety of dicots and obtaining transgenic plants are well documented in the literature (see Gasser. C. S. and Fraley, R. T. (1989) *Science* 244:1293–1299; Fisk, H. J. and Dandekar, A. M. (1993) *Scientia Horticulturae* 55:5–36; Christou (1994) *Agro Food Industry Hi Tech* (March/April 1994) p.17, and the references cited therein).

Successful transformation and plant regeneration have been achieved in the monocots as follows: asparagus (*Asparagus officinalis*; Bytebier et al. (1987) *Proc. Natl. Acad. Sci. USA* 84:5345); barley (*Hordeum vulgarae*; Wan, Y. and Lemaux, P. G. (1994) *Plant Physiol.* 104:37–48); maize (*Zea mays*; Rhodes, C. A. et al. (1988) *Science* 240:204–207; Gordon-Kamm, W. J. et al. (1990) *Plant Cell* 2:603–618; Fromm, M. E. et al. (1990) *Bio/Technology* 8:833–839; Koziel et al. (1993) *Bio/Technology* 11: 194); oats (*Avena sativa*; Somers et al. (1992) *Bio/Technology* 10:1589); orchardgrass (*Dactylis glomerata*; Horn, M. E. et al. (1988) *Plant Cell Rep.* 7:469–472); rice (*Oryza sativa*, including indica and japonica varieties; Toriyama, K. et al. (1988) *Bio/Technology* 6:1072–1074; Zhang, H. M. et al. (1988) *Plant Cell Rep.* 7:379–384; Luo and Wu (1988) *Plant Mol. Biol. Rep.* 6:165; Zhang, W. and Wu, R. (1988) *Theor. Appl. Genet.* 76:835–840; Christou et al. (1991) *Bio/Technology* 9:957); rye (*Secale cereale*; De la Pena et al. (1987) *Nature* 325:274); sorghum (*Sorghum bicolor*; Casas, A. M. et al. (1993) *Proc. Natl. Acad Sci. USA* 90:11212–11216); sugar cane (Saccharum spp.; Bower and Birch (1992) *Plant J.* 2:409); tall fescue (*Festuca arundinacea*; Wang, Z. Y. et al. (1992) *Bio/Technology* 10:691–696); turfgrass (*Agrostis palustris*; Zhong, H. et al. (1993) *Plant Cell Rep.* 13:1–6); and wheat (*Triticum aestivum*; Vasil et al. (1992) *Bio/Technology* 10:667; Weeks, J. T. et al. (1993) *Plant Physiol.* 102:1077–1084; Becker, D. et al. (1994) *Plant J.* 5:299–307).

Particularly useful plants for polyester production include those, such as potato and sugarbeet, that produce carbon substrates which can be employed for polyester biosynthesis. Cereal plants such as corn, wheat, and rice are also preferred. Other useful plants include tobacco and high oil seed plants such as soybean, canola, oil seed rape, Arabidopsis sp. and peanut. Plants that grow in desert or in mineralized soil can also be employed for the production of polyesters. Polymers that can be produced in this manner include but are not limited to for example, polyhydroxybutyrate, and copolymers incorporating both short chain length and medium chain length monomers, such as polyhydroxybutyrate-co-polyhydroxycaproate, polyhydroxycaproate-co-polyhydroxyoctanoate, and polyhydroxyoctanoate-co-polyhydroxydecanoate.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

What is claimed is:

1. A method for the preparation of a polyester, comprising the steps of: culturing recombinant cells wider conditions suitable for the production of the polyester, wherein the recombinant cells have been genetically engineered to express a polyhydroxyalkanoic acid synthase and a fatty acid:acyl-coenzyme A transferase protein under the control of a single promoter.

2. The method of claim 1, wherein the cell is a plant cell, mammalian cell, insect cell, fungal cell, or bacterial cell.

3. The method of claim 2, wherein the cell is a plant cell.

4. The method of claim 2, wherein the cell is a bacterial cell.

5. The method of claim 4, wherein the cell is *Escherichia coli*.

6. The method of claim 5, wherein the bacterial cell is *Escherichia coli* strain XL1-Blue.

7. The method of claim 1, wherein the polyhydroxyalkanoic acid synthase protein is a polyhydroxyalkanoic acid synthase protein from *Alcaligenes eutrophus*.

8. The method of claim 7, wherein the *Alcaligenes eutrophus* polyhydroxyalkanoic acid synthase protein is encoded by the *Alcaligenes eutrophus* polyhydroxyalkanoic acid synthase structural gene.

9. The method of claim 1, wherein the fatty acid:acyl-coenzyme A transferase protein is a 4-hydroxybutyrate:acyl-coenzyne A transferase protein.

10. The method of claim 9, wherein the 4-hydroxybutyrate:acyl-coenzyme A transferase protein is a *Clostridium kluyveri* 4-hydroxybutyrate:acyl-coenzyme A transferase protein.

11. The method of claim 10, wherein the *Clostridium kluyveri* 4-hydroxybutyrate:acyl-coenzyme A transferase protein is encoded by *Clostridium kluyveri orfZ* 4-hydroxybutyrate:acyl-coenzyme A transferase structural gene.

12. The method of claim 1, wherein the culture contains glucose.

13. The method of claim 1, wherein the culture contains materials selected from the group consisting of 4-hydroxybutyric acid, the sodium salt of 4-hydroxybutyric acid, γ-butyrolactone, 1,4-butanediol, 4-hydroxyvaleric acid, γ-valerolactone, 1,4-pentanediol, 3-hydroxybutyric acid, the sodium salt of 3-hydroxybutyric acid, a hydroxypropionic acid, a hydroxybutyric acid, a hydroxyvaleric acid, a hydroxycaproic acid, a hyroxyheptanoic acid, a hydroxyoctanoic acid, a hydroxydecanoic acid, γ-caprolactone, γ-heptanolactone, γ-octanolactone, and γ-decanolactone.

14. The method of claim 1, wherein the culture contains molecular oxygen.

15. The method of claim 1, wherein the cell expresses a heterologous nucleic acid segment encoding a protein capable of hydrolyzing a lactone to the corresponding hydroxyalkanoic acid.

16. The method of claim 1, wherein the cell expresses heterologous nucleic acid segments encoding 2-oxyglutarate decarboxylase protein and a heterologous 4-hydroxybutyrate dehydrogenase protein.

17. The method of claim 1, wherein the cell expresses a hererologous nucleic acid segment encoding a protein selected from the group consisting of a 2-methylcitrate synthase protein, a 2-methylcitrate dehydratase protein, 2-methylisocitrate dehydratase protein, 2-methylisocitrate lyase protein, a succinate:aceyl-CoA transferase protein, a succinate-semialdehyde dehydrogenase protein, and a 4-hydroxybutyrate dehydrogenase protein.

18. The method of claim 1, wherein the cell expresses nucleic acid segments encoding succinate-semialdehyde dehydrogenase protein, and a 4-hydroxybutyrate dehydrogenase protein.

19. The method of claim 1, wherein the cell expresses nucleic acid segments encoding 2-methylisocitrate dehydratase protein, a 2-methylisocitrate dehydratase protein, 2-methylisocitrate dehydratase protein, a 2-methylisocitrate lyase protein, a succinate:acetyl-CoA transferase protein, a succinate-semialdehyde dehydrogenase protein, and a 4-hydroxybutyrate dehydrogenase protein.

20. The method of claim 1, wherein the polyester is a homopolyester.

21. The method of claim 20, wherein the homopolyester is poly(4-hydroxybutyric acid).

22. The method of claim 20, wherein the homopolyester is poly(3-hydroxybutyric acid).

23. The method of claim 1, wherein the polyester is a copolyester.

24. The method of claim 23, wherein the copolyester is poly(3-hydroxybutyric acid-co-4-hydroxybutyric acid).

25. The method of claim 1, further comprising separating the polyester from the recombinant cells.

* * * * *

UNITED STATES PATENT AND TRADEMARK OFFICE
CERTIFICATE OF CORRECTION

| | | |
|---|---|---|
| PATENT NO. | : 6,759,219 B2 | Page 1 of 1 |
| APPLICATION NO. | : 09/380773 | |
| DATED | : July 6, 2004 | |
| INVENTOR(S) | : Silke Hein et al. | |

It is certified that error appears in the above-identified patent and that said Letters Patent is hereby corrected as shown below:

Column 31, line 52, replace "wider" with --under--.

Signed and Sealed this

Tenth Day of July, 2007

JON W. DUDAS
*Director of the United States Patent and Trademark Office*